(12) United States Patent
Segawa et al.

(10) Patent No.: US 9,475,051 B2
(45) Date of Patent: Oct. 25, 2016

(54) NUCLEIC ACID AMPLIFIER

(75) Inventors: Yuji Segawa, Tokyo (JP); Tasuku Yotoriyama, Tokyo (JP); Akio Yasuda, Tokyo (JP); Noriyuki Kishii, Kanagawa (JP); Mayumi Shiono, Tokyo (JP); Takuro Yamamoto, Kanagawa (JP); Tomoteru Abe, Kanagawa (JP)

(73) Assignee: Sony Corporation, Tokyo (JP)

( * ) Notice: Subject to any disclaimer, the term of this patent is extended or adjusted under 35 U.S.C. 154(b) by 1028 days.

(21) Appl. No.: 12/037,619

(22) Filed: Feb. 26, 2008

(65) Prior Publication Data

US 2008/0220509 A1 Sep. 11, 2008

(30) Foreign Application Priority Data

Feb. 27, 2007 (JP) ................................ 2007-046686
Aug. 30, 2007 (JP) ................................ 2007-223494

(51) Int. Cl.
*C12M 1/34* (2006.01)
*B01L 7/00* (2006.01)
*G01N 21/03* (2006.01)
*G01N 21/64* (2006.01)
*B01L 3/00* (2006.01)

(52) U.S. Cl.
CPC ............ *B01L 7/00* (2013.01); *G01N 21/0332* (2013.01); *G01N 21/6428* (2013.01); *G01N 21/6454* (2013.01); *B01L 3/50851* (2013.01); *B01L 7/54* (2013.01); *B01L 2300/0654* (2013.01); *B01L 2300/0819* (2013.01); *B01L 2300/1822* (2013.01); *B01L 2300/1827* (2013.01); *G01N 2021/0325* (2013.01); *G01N 2201/062* (2013.01)

(58) Field of Classification Search
CPC .... C12Q 1/686; C12Q 1/6844; C12Q 1/689; C12Q 1/6853; C12Q 1/6848; C12Q 1/6883; C12Q 1/6827; C12Q 1/6816; C12Q 2600/156; C12Q 1/6869
USPC ...................................................... 435/287.2
See application file for complete search history.

(56) References Cited

U.S. PATENT DOCUMENTS

| | | | |
|---|---|---|---|
| 6,423,948 B1 * | 7/2002 | Kwasnoski et al. | 219/428 |
| 6,504,226 B1 * | 1/2003 | Bryant | 257/510 |
| 2002/0058258 A1 | 5/2002 | Wittwer et al. | |
| 2005/0009070 A1 | 1/2005 | Arciniegas et al. | |

(Continued)

FOREIGN PATENT DOCUMENTS

| | | |
|---|---|---|
| DE | 39 15 920 A1 | 11/1990 |
| JP | 5-317030 | 12/1993 |

(Continued)

OTHER PUBLICATIONS

European Search Report dated Feb. 17, 2010, in EP 08 25 0662.

(Continued)

*Primary Examiner* — Michael Hobbs
(74) *Attorney, Agent, or Firm* — Wolf, Greenfield & Sacks, P.C.

(57) ABSTRACT

A nucleic acid amplifier for carrying out a nucleic acid amplification reaction is disclosed. The amplifier includes a plurality of wells configured to carry out the nucleic acid amplification reaction. The amplifier also include a heating unit provided for every well. The amplifier further includes a light source for irradiating excitation light of a specified wavelength to all of the wells. A fluorescence detection unit is provided for every well.

11 Claims, 2 Drawing Sheets

(56) References Cited

U.S. PATENT DOCUMENTS

| | | |
|---|---|---|
| 2005/0133724 A1 | 6/2005 | Hsieh et al. |
| 2006/0030037 A1 | 2/2006 | Joseph et al. |
| 2006/0073491 A1* | 4/2006 | Joseph et al. ............... 435/6 |
| 2006/0228268 A1 | 10/2006 | Heimberg et al. |
| 2009/0169190 A1* | 7/2009 | Fang et al. ............... 392/485 |

FOREIGN PATENT DOCUMENTS

| | | |
|---|---|---|
| JP | 05-317030 | 12/1993 |
| JP | 10-501616 | 2/1998 |
| JP | 10-501617 | 2/1998 |
| JP | 2000-511629 | 9/2000 |
| JP | 2000-512138 | 9/2000 |
| JP | 2001-136954 | 5/2001 |
| JP | 2003-511221 | 3/2003 |
| JP | 2003-514223 | 4/2003 |
| JP | 2003-525617 | 9/2003 |
| JP | 2005-526975 | 9/2005 |
| JP | 2007-40821 | 2/2007 |
| JP | 2007-040821 | 2/2007 |
| JP | 2008-237207 | 10/2008 |
| JP | 2008-278810 | 11/2008 |
| WO | WO 01/66254 | 9/2001 |
| WO | WO-2005/054458 A1 | 6/2005 |

OTHER PUBLICATIONS

Communication dated Apr. 15, 2011 issued by European Patent Office in European Patent Application No. 08250662.7. (4 pages).
Office Action dated Sep. 11, 2012, in corresponding JP Application 2010-034107.
Translation of JPA/HEI 05-317030, dated Dec. 3, 1993.
Translation of JPT/HEI 10-501616, dated Feb. 10, 1998.
Translation of JPT/HEI 10-501617, dated Feb. 10, 1998.
Translation of JPT 2000-511629, dated Sep. 5, 2000.
Transalation of JPA 2001-136954, dated May 22, 2001.
Translation of JPT 2003-514223, dated Apr. 15, 2003.
Translation of JPT 2005-526975, dated Sep. 8, 2005.
Translation of JPA 2007-40821, dated Feb. 15, 2007.
Translation of JP 4458133, dated Oct. 9, 2008, which corresponds to JP 2008-237207.
Translation of JP 2008-278810, dated Nov. 20, 2008.
Office Action from corresponding Japanese Application No. JP 2010-034107,dated Jul. 23, 2013.
Office Action from corresponding Japanese Application No. JP 2010-034107, dated Dec. 17, 2013.

* cited by examiner

NUCLEIC ACID AMPLIFIER

CROSS REFERENCES TO RELATED APPLICATIONS

The present invention contains subject matter related to Japanese Patent Application JP 2007-223494 filed with the Japan Patent Office on Aug. 30, 2007 and Japanese Patent Application JP 2007-046686 filed with the Japan Patent Office on Feb. 27, 2007, the entire contents of which being incorporated herein by reference.

BACKGROUND OF THE INVENTION

1. Field of the Invention

This invention relates to a nucleic acid amplifier. More particularly, the invention relates to a nucleic acid amplifier and the like used for gene analyses such as gene expression analysis, screening for infectious diseases, SNP analysis and the like.

2. Description of the Related Art

In recent years, hybridization detection techniques including DNA chips or DNA microarrays have been advanced in practice. DNA chips are ones wherein a wide variety of DNA probes are accumulated and fixed on a substrate surface. When this DNA chip is used for detection of hybridization on the DNA chip substrate surface, gene expression in cells, tissues or the like can be comprehensively analyzed.

Data obtained from the microarray is verified by carrying out a nucleic acid amplification reaction such as a PCR (polymerase chain reaction) process or the like. This is a standard technique of qualitative analysis of a trace amount of nucleic acid. Although techniques other than the PCR process have been used as a nucleic acid amplification technique used for the qualitative analysis of a trace amount of nucleic acid, a real time PCR process is illustrated herein by way of an example.

The real time PCR process is a process wherein DNA or the like is amplified to several hundreds of thousands times by continuously conducting an amplification cycle of "thermal denaturation → annealing with a primer → polymerase elongation reaction". The PCR amplified product obtained in this way is monitored in real time to qualitatively analyze such a trace amount of nucleic acid as mentioned above. In this real time PCR process, a dedicated device integrated of a thermal cycler and a spectrophotofluorometer is used to monitor the PCR amplified product in real time.

The detection method of this real time PCR is described below.

Initially, there is mentioned an intercalator method using SYBR (registered trade name) Green I. In the intercalator method, an intercalator having such a property as to emit fluorescence by binding with double-stranded DNA. This intercalator is bound to double-stranded DNA formed during the course of the PCR reaction, against which excitation light is irradiated thereby emitting fluorescence. The detection of this fluorescence intensity enables an amount of the PCR amplified product to be monitored. According to this intercalator method, there is no necessity of designing and synthesizing a fluorescence-labeled probe specific to a target and thus, this method can be simply utilized for the measurement of a variety of targets.

If it is desirable that arrays whose structures are similar to one another be distinctly detected or if multiplex detection is necessary such as for typing of SNPs, a probe method is used. For the probe method, mention is made, for example, of a TaqMan (registered trade name) probe method wherein an oligonucleotide with its 5' terminal modified with a fluorescent substance and 3' terminal modified with a quencher substance is used as probe II.

The TaqMan probe is hybridized specifically to template DNA in an annealing step, under which when excitation light is irradiated, the light is quenched owing to the existence of the quencher substance on the probe, resulting in no emission of fluorescence. However, in the elongation reaction step, the TaqMan probe hybridized to the template DNA is decomposed by the 5'→3' exonuclease activity of the TaqMan polymerase. Eventually, the fluorescent substance is released from the probe, so that the inhibition with the quencher is removed thereby emitting fluorescence. The amount of the PCR amplified product can be monitored by detecting the intensity of the fluorescence.

The procedure of quantitatively determining a gene expression level by the above method using real time PCR is described in more detail. First, PCR is carried out using, as a template, serially diluted standard samples whose concentrations are known to obtain the number of threshold cycles (Ct value) arriving at a given amount of an amplified product. This Ct value is taken as an abscissa and an initial amount of DNA is plotted as an ordinate, thereby providing a calibration curve. Based on this, a sample whose concentration is unknown is subjected to the PCR reaction under similar conditions to obtain a Ct value. An amount of target DNA in the sample is determined from the Ct value and the calibration curve.

Technologies concerning a temperature control and the like at the time of the amplification reaction are disclosed, as techniques concerning the above methods, in JP-A-2003-525617 and Japanese Patent Laid-open No. 2001-136954.

SUMMARY OF THE INVENTION

It is expected for a nucleic acid amplifier to analyze an amount of a target nucleic acid in high accuracy. To this end, an amplification factor of a sample (gene) should be made constant. Accordingly, the invention has for its primary purpose the provision of a nucleic acid amplifier which is able to control an amplification factor of gene in high accuracy.

The invention provides a nucleic acid amplifier adapted to carry out a nucleic acid amplification reaction, the amplifier including at least a plurality of wells for carrying out the nucleic acid amplification reaction, a heating unit provided for every well, optical means capable of irradiating excitation light of a specified wavelength to all of the plurality of wells, and a fluorescence detection unit provided for every well. Since the heating unit and the fluorescence detection unit are both provided for every well, the reaction in the wells can be individually controlled.

Further, the invention provides a nucleic acid amplifier wherein the nucleic acid amplification reaction is carried out, at least, by use of a PCR process. In the PCR process, a nucleic acid is amplified according to a given temperature cycle. The nucleic acid amplifier of the present embodiment is able to control a temperature cycle carried out in the respective wells individually and in high accuracy, ensuring more accurate analysis.

The invention also provides a nucleic acid amplifier wherein the nucleic acid amplification reaction is carried out isothermally. For use as a so-called isothermal nucleic acid amplifier, the temperatures of individual wells are controlled, so that amplification factors of the nucleic acid amplification reactions in the respective wells can be made uniform. As a consequence, using the isothermal amplification method, more accurate analysis becomes possible.

The invention provides a nucleic acid amplifier wherein the heating temperatures and heating times of the wells are individually controlled by means of the heating units corresponding to the respective wells. The control of the heating temperature and heating time of individual wells by use of the corresponding heating units ensures more accurate control such as of the amplification reaction and the like in the wells.

Further, the invention provides a nucleic acid amplifier wherein the heating unit is formed of a thin film transistor and is switch-controlled. Using the switching of the thin film transistor, the temperatures in the respective wells can be individually controlled.

The invention provides a nucleic acid amplifier wherein the heating unit is formed of a heat generation resistor and is switch-controlled with a thin film transistor. Using the switching of the thin film transistor, the temperatures of the respective wells can be individually controlled by controlling a value of current passing through the heat generation resistor.

Moreover, the invention provides a nucleic acid amplifier that is provided with a constant temperature-controlling Peltier element. The use of the Peltier element allows easy temperature control within the well.

The invention provides a nucleic acid amplifier which includes, at least, such optical means as set out hereinabove, a light source emitting excitation light of a specified wavelength, a light guide plate introducing the excitation light to all of the plurality of wells. In this way, the excitation light can be introduced into all the wells from the light source.

The invention also provides a nucleic acid amplifier, which further includes a filter film provided between the well and the fluorescence detection unit and capable of transmitting light of a specified wavelength. The provision of the filter film permits detected fluorescence to be efficiently retrieved.

Further, the invention provides a nucleic acid amplifier, which further includes a filter film provided between the well and the light guide plate and capable of transmitting light of a specified wavelength. The provision of the filter film permits the excitation light to be irradiated to the respective wells to be efficiently retrieved.

Still further, the invention provides a nucleic acid amplifier wherein the light source is made of a light-emitting diode. Use of the light-emitting diode as the light source enables light free of unnecessary ultraviolet light, infrared light and the like to be obtained simply.

Using the nucleic acid amplifier according to the present embodiment, a gene expression level can be comprehensively analyzed in high accuracy.

DETAILED DESCRIPTION OF THE PREFERRED EMBODIMENTS

Figure 1:
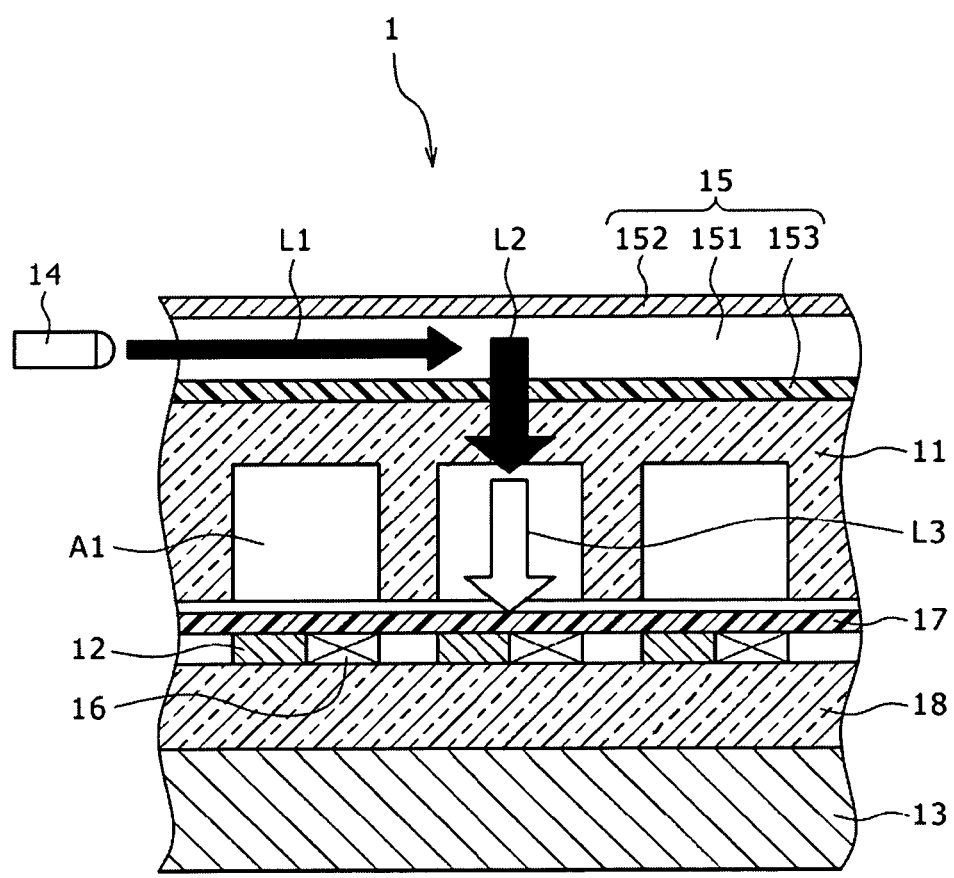
FIG. 1 is a schematic side view showing a nucleic acid amplifier according to a first embodiment of the invention.

Embodiments of the invention are now described with reference to the accompanying drawings. It will be noted that the embodiments shown in the drawings are preferred ones, which should not be construed as limiting the invention thereto.

FIG. 1 is a schematic side view showing a nucleic acid amplifier according to a first embodiment of the invention. It is to be noted that the configuration of an amplifier shown in the figure is shown as simplified for convenience of illustration.

In FIG. 1, a nucleic acid amplifier of the invention is indicated generically as 1. The size and layer structure of the nucleic acid amplifier 1 may be appropriately selected depending on the purpose, and the configuration of the nucleic acid amplifier 1 may be altered in design in the range of purposes of the invention.

The configuration of the nucleic acid amplifier 1 is particularly illustrated. The nucleic acid amplifier 1 includes a reaction substrate 11, a heating unit 12 heating the reaction substrate 11, a Peltier element 13, a light source 14, a light guide plate 15 guiding excitation light to the reaction substrate 11, a fluorescence detection unit 16 detecting fluorescence, a filter film 17 passing only light of a specified wavelength, and a measuring substrate 18.

The reaction substrate 11 has a plurality of wells (reaction regions) A1 and a given reaction is carried out within the well A1. In the practice of the present embodiment, the well A1 is not critical with respect to the shape or the like and may appropriately have a favorable shape and capacity.

The capacity of the well A1 is not critical and is preferably a microspace. In particular, the capacity is preferably at 1 µl or below. Such a microspace is advantageous in that a reaction solution necessary for the well A1 is so small in amount that the temperature control or the like can be made in high accuracy and the reaction time can be shortened.

For instance, if the well A1 is so dimensioned as to be at 300 µm×300 µm×300 µm (well capacity of 27 nl) and about forty thousands of wells A1 are set up in the reaction substrate 11, the area necessary for the device is at about 6 cm square. In this way, since miniaturization of the device is possible, a number of wells A1 comparable to the number of human genes can be arranged in matrix on the reaction substrate 11, thereby permitting exhaustive analyses to be conducted easily and simply.

The reaction substrate 11 is not critical with respect to the type of material so far as it is able to allow transmission of excitation light L1, and such a material can be appropriately selected in consideration of the purpose in measurement and ease in processability. For example, low fluorescene emitting plastics and glasses and the like can be used as the material of the reaction substrate 11.

Also, the reaction substrate 11 may be detachable from the heating unit 12, the fluorescence detection unit 16, the filter film 17 and the like. Or, not shown in the drawings, the reaction substrate 11 and the heating unit 12 are provided as an integral structure and may be detachable.

The heating units 12 heat individual wells A1 in the reaction substrate 11. Thus, the well A1 is controlled in temperature. It is preferred that the wells A1 are individually controlled by corresponding heating units 12 with respect to the heating temperature and heating time of the well A1. The individual control of the heating temperature and heating time of every well A1 by means of the heating unit 12 ensures more accurate control such as of an amplification reaction and the like in the well A1.

The temperature control such as by a thermal cycler or the like used in the real time PCR process in the past has a problem in that the respective samples may not be individually controlled in temperature although a gradient mechanism may be added in some case. In contrast thereto, according to the present embodiment, since the heating units 12 are provided for the respective wells A1, the wells can be independently controlled in temperature. Moreover, the heating units 12 are provided correspondingly to the respective wells A1, so that the heating time can be individually controlled in the course of the amplification reaction.

The heating unit 12 is not critical with respect to the structure, and is preferably a heater that is formed of a thin film transistor (TFT) and is switch-controlled. Using the switching function of a thin film transistor, the respective wells A1 can be individually controlled in temperature. The temperature control may be made either by controlling a voltage applied to a thin film transistor to make a current between the source and drain variable or by controlling a current between the source and drain as a constant current power supply. Especially, it is preferred to use a thin film transistor as a heating source and another thin film transistor as a switching element so as to form these thin film transistors in the same circuit. This allows package control of the heat source and switching in the same circuit.

Alternatively, the heating unit 12 may be a heater that is formed of a heat generation resistor and is switch-controlled with a thin film transistor. More particularly, the thin film transistor may be used only for switching control. For the heat generation resistor, there may be used platinum (Pt), molybdenum (Mo), tantalum (Ta), tungsten (W), silicon carbide, molybdenum silicide, nickel-chromium alloys, iron-chromium-aluminium alloys and the like. In this case, the control of a value of current passing through the heat generation resistor enables temperature control.

The type of thin film transistor used in the present embodiment is not critical, and polysilicon, a-silicon and the like may be appropriately used for this.

In the practice of the present embodiment, it is preferred to provide a Peltier element 13 so as to conduct the temperature control of the well A1. The wells are controlled in temperature as a whole by means of the Peltier element and the temperatures of the respective wells A1 can be more precisely controlled by means of the respective heating units 12. In this manner, the respective wells A1 can be precisely controlled without involving a minute variation or deviation of temperature. Using the Peltier element 13, the constant temperature control can be readily made. As a result, the temperature control of high accuracy can be performed.

Where the PCR cycle is performed, it is necessary to carry out the temperature control according to the steps of "thermal denaturation → annealing (hybridization of a primer) → elongation reaction). For example, the temperature within the well A1 can be maintained at a minimum temperature (e.g. 55° C.) of the PCR cycle beforehand. The temperature cycle of the wells is totally controlled by means of the Peltier element 13 and the variation or deviation of temperature of the respective wells A1 can be individually corrected or controlled by means of the respective heating units 12. In this way, the temperature control of the well as a whole and the temperature control of individual wells are made, respectively, to ensure more accurate temperature control.

In the present embodiment, as optical section capable of irradiating excitation light of a specified wavelength to all of the plurality of wells A1, there may be used either the light source 14 or the light guide plate 15 introducing the excitation light to the wells A1.

The light source 14 may be one which is able to emit light of a specified wavelength and is not critical in type. Preferably, it is preferred to use a light-emitting diode (LED) emitting white or monochromatic light. The use of the light-emitting diode enables light free of unnecessary UV or IR light to be simply obtained.

In the practice of the present embodiment, the installation location of the light source 14 and the number thereof are not critical. Although not shown in the figure, there may be used a structure in which a plurality of light sources 14 corresponding to the number of the wells A1 are provided and excitation light is directly irradiated to the respective wells 14 from the corresponding light sources 14. In this case, for example, since individual wells A1 are directly irradiated with the corresponding light sources, an excitation light level can be made higher, or excitation light levels can be individually controlled to allow uniform excitation irradiation on all the wells.

The light guide plate 15 is one that serves to introduce excitation light L1 emitted from the light source 14 to individual wells A1 in the reaction substrate 11. The excitation light L1 emitted from the light 14 is introduced to a spacer 151 inside the light guide plate 15. A reflection film 152 is disposed at the upper portion of the light guide plate 15. For example, a dichroic mirror or the like can be used to introduce the excitation light L2 to the reaction substrate 11. Hence, a fluorescent substance in a reaction solution placed in the respective wells A1 can be excited by application of a uniform amount of light.

In the practice of the present embodiment, it is preferred to provide, at the bottom of the light guide plate 15, a filter film 153 capable of transmitting only wavelength lights of excitation lights L1, L2. This permits excitation light L2 to be efficiently retrieved from the light emitted from the light source 14 and introduced to the well A1. For the filter film 153, there may be used, for example, a polarizer filter or the like.

The fluorescence detection unit 16 detects and measures fluorescence that is emitted by excitation of a fluorescent dye in an intercalated probe in response to the excitation light L2 irradiated to the well A1. In the present embodiment, the configuration of the fluorescence detection unit 16 or the like is not critical and, for example, a photodiode may be used.

The fluorescence detection unit 16 is formed on the same glass substrate as the heating unit 12 and may be formed on a different substrate or may be in such a state that the heating unit 12 and the fluorescence detection unit 16 are stacked.

In the practice of the present embodiment, it is preferred to provide a filter film 17 capable of transmitting only the wavelength light of the fluorescence L3 between each well A1 and a corresponding fluorescence detection unit 16. The provision of the filter film 17 transmitting only light of a given wavelength between the well A1 and the fluorescence detection unit 16 results in efficient retrieval of detected fluorescence L3, ensuring analysis of higher accuracy. For this filter film 17, there may be used, for example, a polarizer filter or the like.

Since the nucleic acid amplifier 1 of the present embodiment has the fluorescence detection unit 16, fluorescence can be detected in real time. The fluorescence detection units 16 are individually provided correspondingly to the respective wells A1 and thus, the detection with individual wells A1 in high accuracy becomes possible.

Since the fluorescence detection in real time is possible, the results of the detection with the fluorescence detection unit 16 can be fed back to a temperature control mechanism of the heating unit 12. For instance, based on the results of the reaction (i.e. a gene amplification level) of the well A1 detected at the fluorescence detection unit 16, the amount of heat of the heating unit 12 can be designed as controlled. In this way, the results of the detection with the fluorescence detection unit 16 are fed back to the heating unit 12, thereby enabling the gene amplification reaction of the respective wells A1 to be controlled in high accuracy.

The heating unit 12 and the fluorescence detection unit 16 may be provided on the measuring substrate 18. In the present embodiment, the position at which the measuring substrate 18 is provided is not limited to below the heating unit 12 and the fluorescence detection unit 16 and may be arbitrarily determined. The materials of the measuring substrate 18 used in the present embodiment are not critical in type, and glass substrates and various types of resin substrates may be used, for example.

In the nucleic acid amplifier 1 of the present embodiment, an ordinarily employed PCR process can be carried out. In particular, using (1) a target DNA to be amplified, (2) at least two types of oligonucletide primers specifically bound to the target DNA, (3) a buffer solution, (4) an enzyme, (5) a deoxyribonucleotide triphosphate such as dATP, dCTP, dGTP, dTTP or the like, a cycle of "thermal denaturation → annealing (hybridization of primers) → elongation reaction" is repeated to amplify the target DNA to a desired level.

An instance of a measuring procedure using the nucleic acid amplifier 1 according to the present embodiment is now described.

Primers having preliminarily designed, different base sequences are charged into the respective wells A1. The manner of the charge is not critical, for which a method using, for example, an ink jet system can be used. Solutions containing different types of primers are dropped into the respective wells A1 and dried.

Subsequently, total DNA extracted from an analyte is transcribed to cDNA according to a reverse transcription method, followed by charging into the respective wells A1. Simultaneously, a deoxynucleotide triphosphate (dNTP) serving as a starting material for the respective bases necessary for amplification, an intercalator ("SYBR (registered trade name) Green I"), an enzyme DNA polymerase necessary for the DNA elongation amplification reaction and the like are charged.

The nucleic acid amplifier 1 of the present embodiment may be used as a real time PCR device wherein the RT-PCR reaction (reverse transcriptase polymerase chain reaction) is carried out. In an ordinary PCR process, DNA polymerase is used and amplification may not be made if RNA is an object to be analyzed. In contrast thereto, although the RT-PCR process is one wherein PCR is carried out after reverse transcription of RNA into DNA by means of reverse transcriptase, even the RT-PCR reaction can be performed when using the nucleic acid amplifier 1 of the present embodiment.

In order to prevent DNA fragments, which are not intended for in the PCR process, from being amplified, a nested primer may be used (nested PCR method). Where the PCR process is carried out using the nucleic acid amplifier 1 of the present embodiment, it may be as a matter of course to use the RT-PCR process and the nested-PCR process in combination.

In the thermal denaturation step, the heating units 12 are so set that the wells A1 are kept at 95° C. in the inside thereof, in which double-stranded DNA is denatured into single-stranded DNA. In a subsequent annealing step, the wells A1 are so set as to be kept at 55° C., under which a primer is bound in complementary base sequence with the single-stranded DNA. In a next DNA elongation step, the wells A1 are so set as to be at 72° C., under which the polymerase reaction is permitted to proceed using the primer for the initiation of DNA synthesis, thereby causing cDNA to be elongated.

In every temperature cycle of "95° C. (thermal denaturation) → 55° C. (hybridization of primers) → 72° C. (DNA elongation)", cDNA in the respective wells A1 is doubly amplified. The temperature inside the respective wells A1 can be controlled at an optimum value for the designed primer reaction by means of the heating units 12 disposed in the respective wells A1. Also, the time of hybridization of primers and the time of the polymerase reaction can be controlled, thereby controlling the generation of unnecessary by-products. As a result, the amplification factor of cDNA in the respective wells A1 can be kept constant and carried out the PCR reaction with high accuracy.

SYBR Green I intercalates to the ds-DNA produced upon replicative reaction of DNA. This SYBR Green I is a substance that intercalates to ds-DNA and subsequently emits fluorescence by irradiation and excitation with excitation light L2 (excitation light wavelength: 497 nm, emission light wavelength: 520 nm).

In this manner, at the time when DNA is replicated with the DNA polymerase, light L1 from the light source 14 serves to excite the intercalated SYBR Green I through the light guide plate 15 as excitation light L2, thereby emitting fluorescence L3. The amount of this emitted fluorescence L3 is measured with the fluorescence detection unit 11 in every temperature cycle and qualitatively determined. Based on the interrelation between the temperature cycle and a corresponding amount of emitted fluorescence, the amount of initial cDNA as a gene expression level can be obtained.

Figure 2:
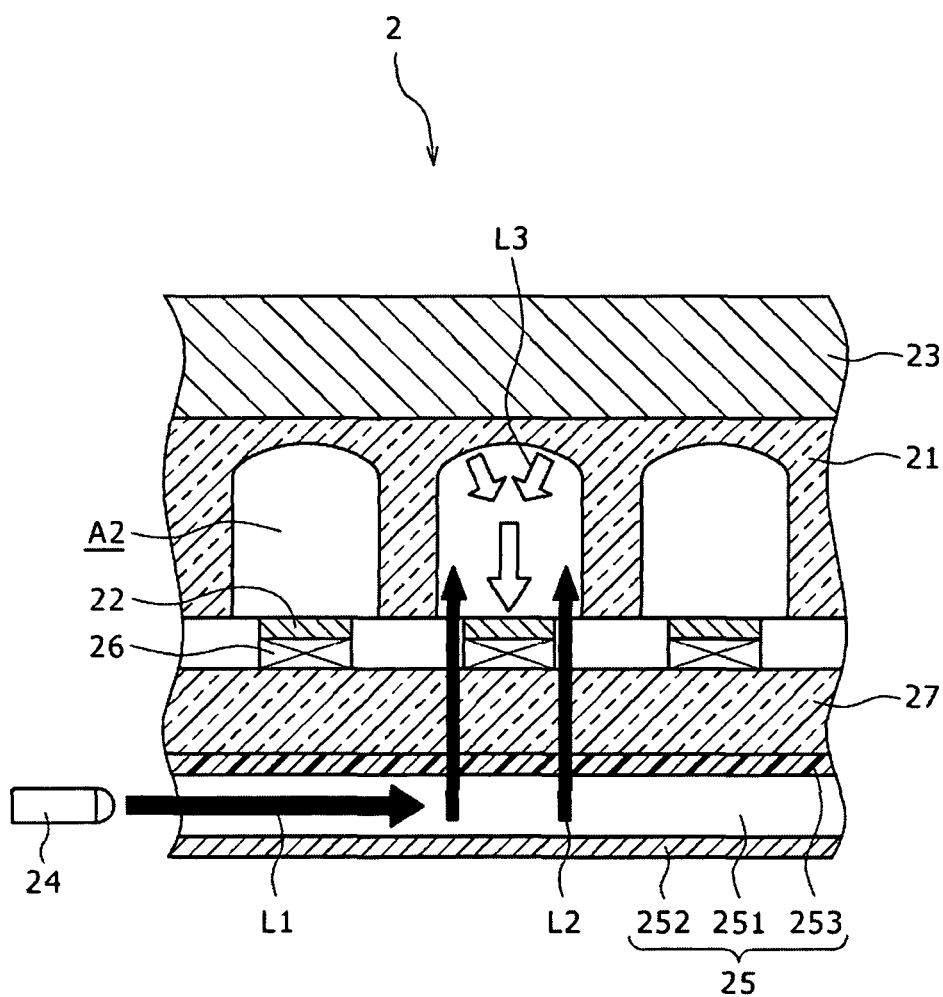
FIG. 2 is a schematic side view showing a nucleic acid amplifier according to a second embodiment of the invention.

FIG. 2 is a schematic side view of a nucleic acid amplifier according to a second embodiment of the present invention. Differences from the first embodiment are mainly illustrated and common portions are not described again.

In FIG. 2, a nucleic acid amplifier indicated at 2 includes a reaction substrate 21, a heating unit 22 heating the reaction substrate 21, a Peltier element 23, a light source 24, a light guide plate 25 leading excitation light to the reaction substrate 21, a fluorescence detection unit 26 detecting fluorescence, and a measuring substrate 27.

This nucleic acid amplifier 2 is common with the first embodiment in that it includes the heating unit 22 and the fluorescence detection unit 26 for every well A2. However, a difference resides in that excitation light L2 is irradiated from below the reaction substrate 21 and is reflected within the well A2 to detect fluorescence L3. In doing so, the well A2 is so shaped as having a curved portion at which the fluorescence L3 is reflected.

With the nucleic acid amplifier 2, excitation light L1 emitted from the light source 24 is irradiated to the well A2 through the light guide plate 25. In the light guide plate 25, excitation light L1 passes a spacer 251 and excitation light L2 is introduced to the reaction substrate 21 through a reflection film 252 and a filter film 253. The excitation light L2 is irradiated to a fluorescent substance serving as a probe in a reaction solution within the well A2, whereupon fluorescence L3 is emitted. This fluorescence L3 is reflected at the wall surface in the well A2 and is detected and measured with the fluorescence detection unit 26 provided below the well A2.

The temperature control is performed by means of the heating unit 22 provided below the well A2, and the temperature can be controlled such as with the Peltier element 23.

In an ordinary real time PCR device, the cycle composing of "thermal denaturation→annealing→elongation reaction" is repeated about 30 cycles, for which it takes 25 to 30 minutes for the reaction. During the cycles, a temperature control of about 2° C./second is performed. In contrast, with the device of the present embodiment, a temperature control of not lower than 20° C./second is possible, so that the time could be shortened by about 40 seconds per cycle. As to 30 cycles in total, a reaction time of not longer than about 25 minutes can be achieved.

In the nucleic acid amplifier of the present embodiment, when the heating unit and the fluorescence unit are, respectively, set for every well, individual wells can be independently controlled with respect to the heating temperature and heating time, thus enabling individual detection. Thus, analysis of an gene expression level or the like in high accuracy can be made within a short time.

Further, if the fluorescence detection unit is provided as a device integrated with an excitation optical system, miniaturization as a detection system is possible. If the well is formed as a microspace so that the reaction region is made small, comprehensive analysis can be effected in an efficient manner although the device is small in size. Hence, the nucleic acid amplifier of the present embodiment enables comprehensive analysis.

The nucleic acid amplifier of the present embodiment can be used as an isothermal nucleic acid amplifier for carrying out the nucleic acid amplification reaction isothermally. The term "isothermal" means substantially constant temperature conditions where an employed enzyme or primer is substantially functional. The term "substantially constant temperature conditions" encompasses not only to strictly keep a preset temperature, but also to keep a temperature variation to an extent not impeding a substantial function of an employed enzyme and primer within an allowable temperature range.

In the practice of the present embodiment, the following isothermal amplification methods can be used aside from the PCR process having described hereinbefore.

That is, mention is made of an IVT (In Vitro Transcription) process wherein RNA is obtained dsDNA as an amplified product, a TRC (Transcription Reverse transcription Concerted amplification) process wherein RNA is trimmed by use of the RNase H activity of a reverse transcriptase to obtain RNA as an amplified product), an NASBA (Nucleic Acid sequence-Based Amplification) process wherein a reverse transcriptase is used to provide a RNA promoter-incorporated dsDNA and RNA is obtained from the dsNDA as an amplified product by use of an RNA polymerase, a SPIA process wherein using a primer made of a chimeric structure of RNA and DNA, ssDNA is obtained from RNA as an amplified product, a LAMP (Loop-Mediated isothermal Amplification) process wherein using loop formation of DNA, dsDNA is obtained from DNA and RNA as an amplified product at a constant temperature, a SMAP (SMart Amplification) process wherein using a plurality of enzymes in combination, dsDNA is obtained from dsDNA as an amplified product while accurately discriminating a difference of one base (SNP), an ICAN (Isothermal and Chimeric pr-mer-initiated Amplification of Nucleic acids) process wherein using a synthetic chimeric primer of DNA and RNA being bound together, dsDNA is obtained from dsDNA as an amplified product, and the like.

It is as a matter of course that the isothermal amplification processes which may be carried out according to the present embodiment are not limited to those isothermal amplification processes set out above, and the above-mentioned processes should not be construed as limited only to such contents as set forth above. More particularly, the isothermal amplification process which may be carried out by the present embodiment encompasses all processes wherein a nucleic acid is amplified without resorting to any temperature cycle.

Because of no necessity of such a temperature cycle (e.g. 95° C.→55° C.→72° C.) as in the afore-described PCR process, the isothermal amplification processes are advantageous in that no device such as a thermal cycler is necessary. However, a difference in amplification factor depending on the structure and chain length of a nucleic acid to be amplified is caused, making it difficult to effect quantitative analysis.

In this regard, according to the nucleic acid amplifier of the present embodiment, the reaction temperatures of the respective wells can be individually controlled to correct a difference in amplification factor of nucleic acids in the respective wells. Hence, the reaction efficiencies of the nucleic acid amplification reaction in the respective wells can be kept constant. As a result, even if a plurality of nucleic acid amplification reactions are conducted in a plurality of wells, amounts of amplified nucleic acids in the respective wells can be quantitatively known from one calibration curve. Accordingly, using the nucleic acid amplifier of the present embodiment, an expression level can be quantitatively analyzed.

Further, where appropriate reaction temperature conditions, under which a predetermined nucleic acid amplification reaction is carried out, are not known, an appropriate reaction temperature is fed back from the initial results of the amplification reaction, thereby enabling the reaction efficiency of the nucleic acid amplification reaction to be kept constant. More particularly, the interrelation between the amplification level and the temperature at the level is detected within a given time from the initiation of the amplification reaction. The results of the detection are fed back to the temperature control mechanism of the heating unit, with which appropriate reaction temperature conditions for carrying out the amplification reaction can be determined.

Where a quantitative reaction is carried out, the isothermal amplification process is more difficult in application than the PCR process. The main reason for this resides in a great difference in amplification factor, which depends on the structure and chain length of a nucleic acid to be amplified. In the quantitative analysis using the nucleic acid amplification reaction, comparison with a reference having an identical amplification factor is necessary, so that such a difference in amplification factor makes the quantitative analysis difficult. Especially, where a number of genes are quantitatively determined at the same time, a difficulty is involved in making a calibration curve for every target nucleic acid and it is necessary to compare nucleic acids whose amplification factors are coincident with each other.

In contrast, with nucleic acid amplifier of the present embodiment, even if a nucleic acid is amplified according to the isothermal amplification process, the amplification reaction can be carried out at an optimum temperature corresponding to the type of gene or primer to be amplified. Accordingly, the amplification factors of nucleic acids in the respective wells can be controlled at a constant level. As a result, using the thermal amplification process, quantitative analysis of high accuracy can be made.

The reaction is isothermally carried out, for which no configuration such as of a thermal cycler controlling a temperature cycle is necessary. This contributes more to miniaturization as a device. In addition, the amounts of a great number of genes can be comprehensively analyzed on the same device. Accordingly, the nucleic acid amplifier of the present embodiment may take a form of a chip or substrate provided with microflow paths and may be provided as a high throughput gene analyzer wherein an isothermal amplification process can be performed.

It should be understood by those skilled in the art that various modifications, combinations, sub-combinations and alterations may occur depending on design requirements and other factors insofar as they are within the scope of the appended claims or the equivalents thereof.

What is claimed is:

1. A nucleic acid amplifier for carrying out a nucleic acid amplification reaction, the amplifier comprising:
    a plurality of wells configured to carry out the nucleic acid amplification reaction;
    a heating unit provided for every well;
    an optical unit for irradiating excitation light of a specified wavelength to each of said wells; and
    a fluorescence detection unit provided for every well, each fluorescence detection unit configured to provide a detection result to the respective heating unit,
        wherein the respective heating unit is configured to control the temperature of the nucleic acid amplification reaction in one of the plurality of wells based on at least the detection result from the fluorescence detection unit.

2. The nucleic acid amplifier according to claim 1, wherein said nucleic acid amplification reaction is carried out at least according to a PCR (polymerase chain reaction) process.

3. The nucleic acid amplifier according to claim 1, wherein said nucleic acid amplification reaction is carrier out isothermally.

4. The nucleic acid amplifier according to claim 1, wherein a heating temperature and heating time of said wells are individually controlled by means of said heating units corresponding to the respective wells.

5. The nucleic acid amplifier according to claim 1, wherein said heating unit is formed of a thin film transistor and is switch-controlled.

6. The nucleic acid amplifier according to claim 1, wherein said heating unit is formed of a heat generation resistor and is switch-controlled.

7. The nucleic acid amplifier according to claim 1, further comprising a Peltier element for constant temperature control.

8. The nucleic acid amplifier according to claim 1, wherein said optical unit comprises at least a light source emitting excitation light of a specified wavelength, and a light guide plate introducing said excitation light into the respective wells.

9. The nucleic acid amplifier according to claim 1, further comprising a filter film transmitting light of a specified wavelength provided between said well and said fluorescence detection unit.

10. The nucleic acid amplifier according to claim 8, further comprising a filter film transmitting light of a specified wavelength provided between said well and said light guide plate.

11. The nucleic acid amplifier according to claim 8, wherein said light source is a light emission diode.

* * * * *